(12) United States Patent
Maresh (10) Patent No.: US 10,702,312 B1
(45) Date of Patent: Jul. 7, 2020

(54) SPINAL STABILIZATION APPARATUS

(71) Applicant: Joseph D Maresh, West Linn, OR (US)

(72) Inventor: Joseph D Maresh, West Linn, OR (US)

( * ) Notice: Subject to any disclaimer, the term of this patent is extended or adjusted under 35 U.S.C. 154(b) by 0 days.

(21) Appl. No.: 15/221,592

(22) Filed: Jul. 27, 2016

Related U.S. Application Data (60) Provisional application No. 62/282,187, filed on Jul. 27, 2015.

(51) Int. Cl.
*A61B 17/70* (2006.01)
*A61F 2/44* (2006.01)

(52) U.S. Cl.
CPC .......... *A61B 17/7049* (2013.01); *A61F 2/442* (2013.01); *A61F 2/4405* (2013.01); *A61F 2230/0032* (2013.01)

(58) Field of Classification Search
CPC ............ A61B 17/7005; A61B 17/7011; A61B 17/7013; A61B 17/7022; A61B 17/7019; A61B 17/7023; A61B 17/7026
See application file for complete search history.

(56) References Cited

U.S. PATENT DOCUMENTS

| | | | |
|---|---|---|---|
| 2010/0249845 A1* | 9/2010 | Meunier | A61B 17/7011 606/263 |
| 2013/0103091 A1* | 4/2013 | Acosta, Jr. | A61B 17/7013 606/259 |

* cited by examiner

*Primary Examiner* — Julianna N Harvey
(74) *Attorney, Agent, or Firm* — Nick A Nichols, Jr.

(57) ABSTRACT

A dynamic spinal stabilization apparatus may be implanted and secured to at least two vertebrae. The spinal stabilization apparatus may promote and enforce a relatively natural motion of spine flexion of one or more regions of the spine. In one embodiment, the spinal stabilization apparatus may be secured to a plurality of vertebrae and biasing the entire spine to a fully normal curvature. The spinal stabilization apparatus may dynamically stabilize the spine while preserving spinal motion. In other embodiments, the spinal stabilization apparatus may be utilized for spine fusion treatments and may provide load sharing either as an enhancement to a fusion device or as a motion-preserving non-fusion apparatus.

10 Claims, 7 Drawing Sheets

SPINAL STABILIZATION APPARATUS

CROSS-REFERENCE TO RELATED APPLICATION

This application claims the benefit of U.S. Provisional Application Ser. No. 62/282,187, filed Jul. 27, 2015, which application is incorporated herein in its entirety by reference.

BACKGROUND

The present invention generally relates to the treatment of spinal column disorders including scoliosis, kyphosis, excess lordosis, and spondylolisthesis, which occur relatively frequently and are caused generally by abnormalities, disease, or trauma. Patients that suffer from such conditions usually experience extreme and debilitating pain, as well as diminished nerve function. These spinal disorders, pathologies, and injuries limit the spine's range of motion, and/or threaten the critical elements of the nervous system housed within the spinal column.

Medical systems to treat such disorders continues to advance in both apparatus designs, materials, and methods. Common treatment methods primarily involve a rigid connection apparatus such as solid bars and the like followed by fusion of vertebras, however an emergence of dynamic treatment is occurring where relative movement of vertebras is allowed in instances where fusion is not necessary.

SUMMARY

A dynamic spinal stabilization apparatus may be implanted and secured to at least two vertebrae. The spinal stabilization apparatus may promote and enforce a relatively natural motion of spine flexion of one or more regions of the spine. In one embodiment, the spinal stabilization apparatus may be secured to a plurality of vertebrae and biasing the entire spine to a fully normal curvature. The spinal stabilization apparatus may dynamically stabilize the spine while preserving spinal motion. In other embodiments, the spinal stabilization apparatus may be utilized for spine fusion treatments and may provide load sharing either as an enhancement to a fusion device or as a motion-preserving non-fusion apparatus.

BRIEF DESCRIPTION OF THE DRAWINGS

So that the manner in which the above recited features, advantages and objects of the present invention are attained can be understood in detail, a more particular description of the invention briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

DETAILED DESCRIPTION

Figure 1:
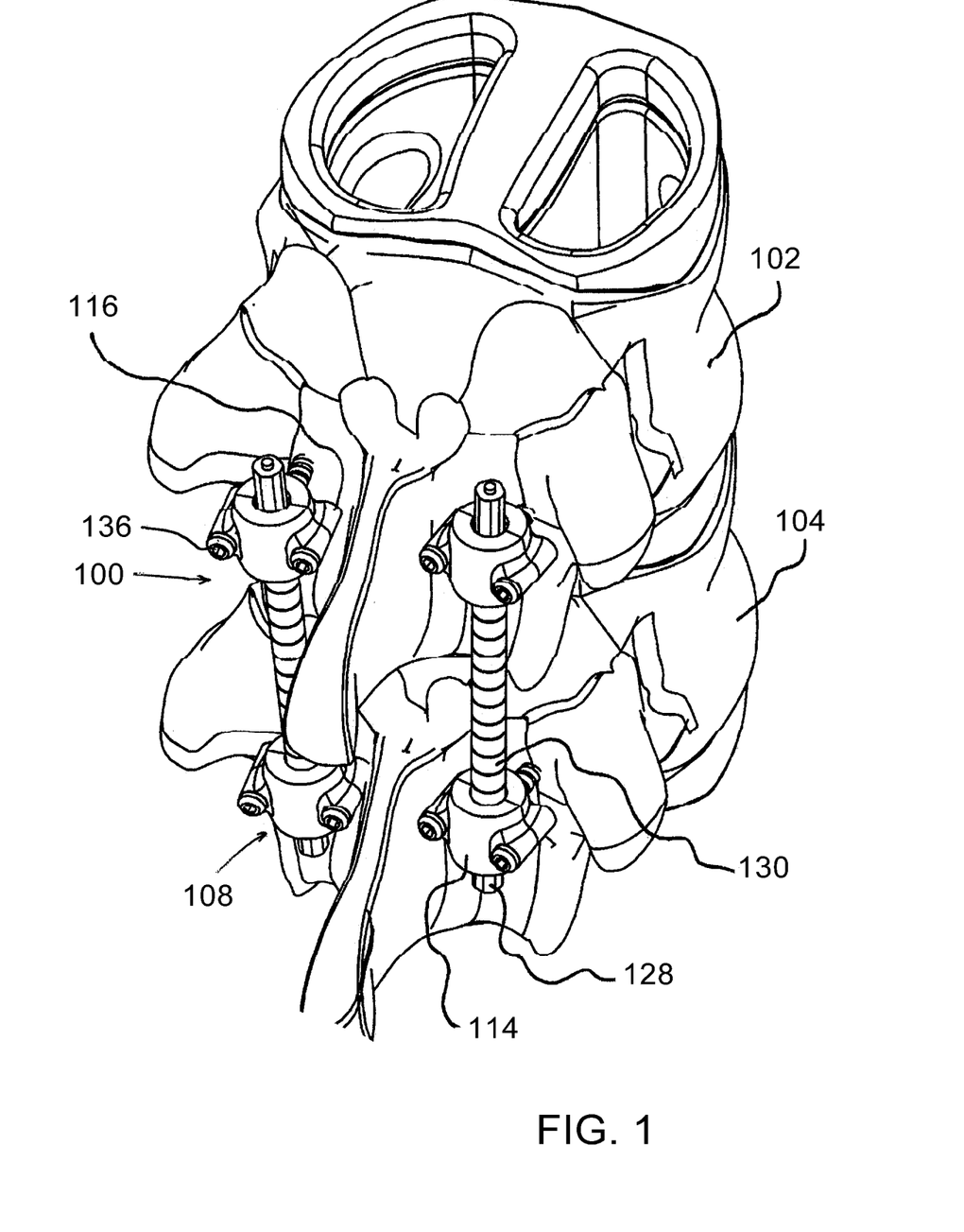
FIG. 1 is a perspective view of a spinal stabilization apparatus secured to spine vertebrae.

Referring first to FIG. 1, a spinal stabilization apparatus is generally identified by reference numeral 100. The spinal stabilization apparatus 100 is depicted coupling two spinal segments or vertebra 102 and 104 together.

The spinal stabilization apparatus 100 may include two or more anchor assemblies 108 securing the spinal stabilization apparatus 100 to the spine vertebra. The anchor assemblies 108, best shown in the exploded view of FIG. 3, may include a pedicle screw 110 adapted to be attached to spine vertebra to a predetermined depth and angle in a manner known in the art. Each anchor assembly 108 may include a socket 112 fixed to or integrally formed with the pedicle screw 110. The socket 112 may be split into two separable parts, including an upper portion or socket cap 114 and a lower portion or socket bottom 116 fixedly secured to an upper distal end of the pedicle screw 110. Upon assembly, the socket cap 144 and socket bottom 116 may collective define a cavity or chamber 118. The chamber 118 may include spaced apart transverse end walls 120 defining opposite ends of the chamber 118. The walls 120 include an opening 122 axially aligned with one another.

Figures 2, 3:
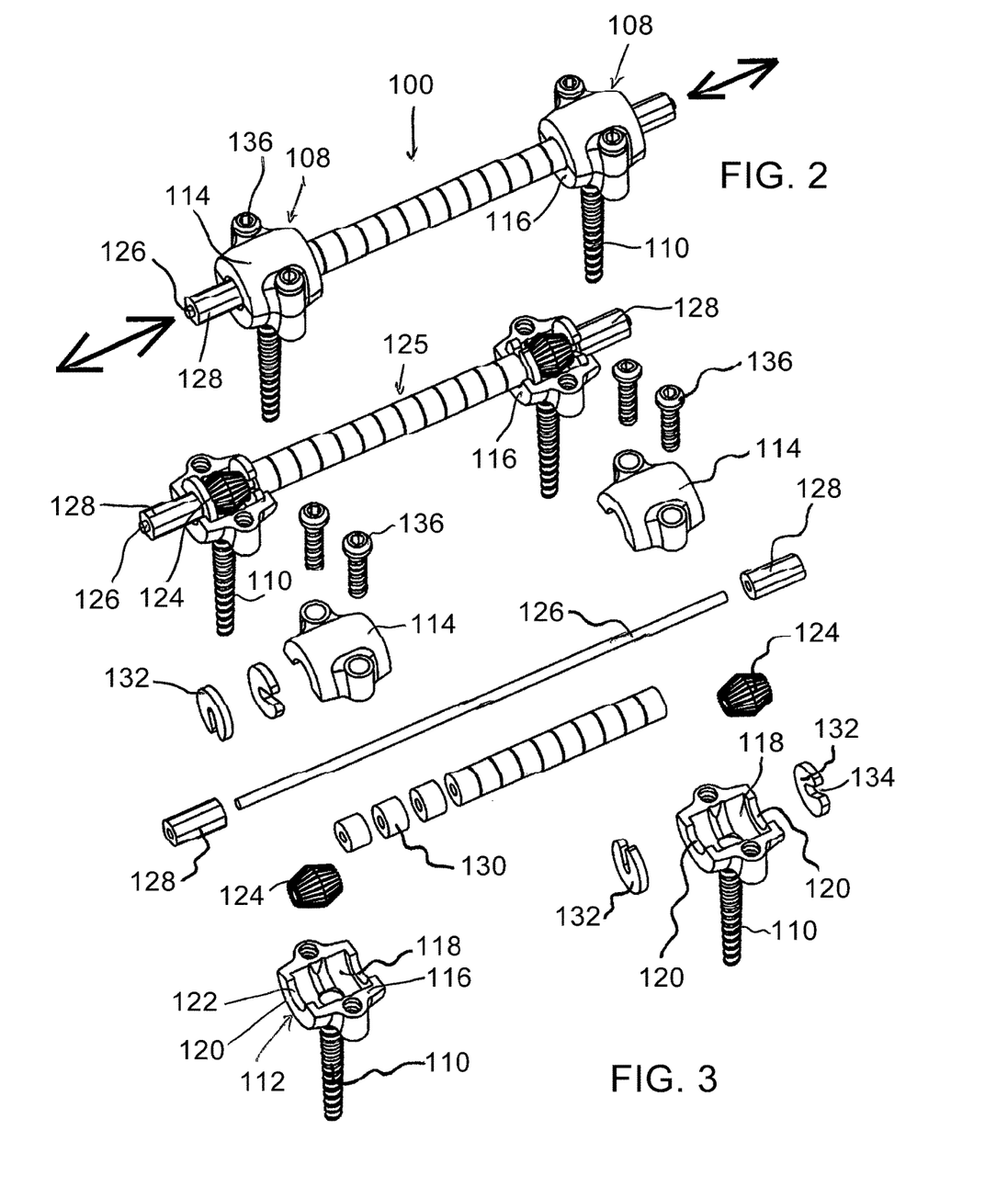
FIG. 2 is a perspective view of the spinal stabilization apparatus illustrated in FIG. 1/
FIG. 3 is an exploded perspective view of components of the spinal stabilization apparatus illustrated in FIG. 1.

The chamber 118 of each socket 112 may be sized and configured to house a spring 124 disposed between the end walls 120 of the chamber 118. The spring 124 may be, for example and without limitation, a polymer compression spring comprised of urethane and/or silicone and the like with spring rates of K=1000 pounds per inch, and where a typical maximum spring deflection may be about 0.150 inch. Alternatively, for example and without limitation, the spring 124 may comprise helical metal compression springs, belleville springs and/or belleville spring washers and the like.

Referring still to FIG. 3, the spinal stabilization apparatus 100 may include a cable sub-assembly 125 comprising a longitudinal tensile member, such as a cable 126, with end bushings 128 fixedly secure at opposite distal ends thereof. The end bushings 128 may be mechanically crimped to the cable 126 in a manner known in the art, where a typical pull test value of the crimp may be approximately equal to the breaking strength of the cable 126 in tension. The cable 126 may be, for example and without limitation, stainless steel 316L or titanium of 1×7, 1×19, 7×7 or 7×19 construction and 3/32 inch in diameter.

Prior to attaching the end bushings 128 to the cable 126, a plurality of bushings 130 may be threaded on the cable 126 in series and. compression springs 124 may be threaded on the cable 126 so that the bushings 130 are disposed between the compression springs 124. Thereafter, the compression springs 124 may be positioned in the socket bottom 116 of respective sockets 112. Washers, for example and without limitation, thrust washers 132, may be inserted between the compression spring 124 and end walls 120 of the socket bottoms 116. The washers 132 may include a radial slot 134 so that the washers 132 may be installed after the end bushings 128 are crimped on the distal ends of the cable 126.

Alternatively, those of ordinary skill in the art will appreciate that the washers 132 may take the form of disks with a hole for threading the washers 132 on the cable 126 with the compression springs 124 disposed between washers 132 and then positioned in the socket bottoms 116 followed by the installation of socket caps 114 by tightening of cap screws 136.

Referring now to FIG. 1, the use of two spinal stabilization apparatus 100 connecting two adjacent vertebrae is illustrated. Initially, the cable sub-assembly 125 comprising the cable 126, bushings 130, compression springs 124, thrust washers 132 and end bushings 128 are assembled and the cable 126 tensioned to a desire tension. The pedicle screws 110 are secured at a predetermined depth and angle to vertebra 102 and 104. The cable sub-assembly may then be installed by placement of the compression springs 124 and thrust washers 132 in respective socket bottoms 116 and securing the socket caps 114 to the socket bottoms 116.

Figure 4A:
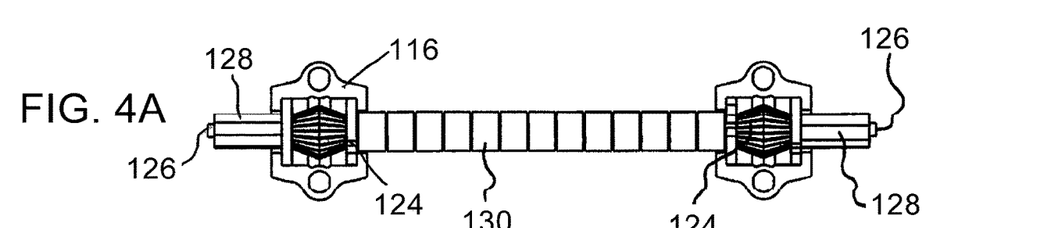
FIGS. 4A-4E are cross section view of the spinal stabilization apparatus illustrated in FIG. 1 depicting configurations of the spinal stabilization apparatus under various vertebrae movements.

In FIGS. 4A-4E, the dynamic functionality of the spinal stabilization apparatus 100 is illustrated. The spinal stabilization apparatus 100 promotes and enforces a relatively natural motion of spine flexion of one or more regions of the spine. In FIG. 4A, the anchor assemblies 108 (and associated vertebrae regions) are generally unbiased and the compression springs 124 are not compressed.

Figure 4B:
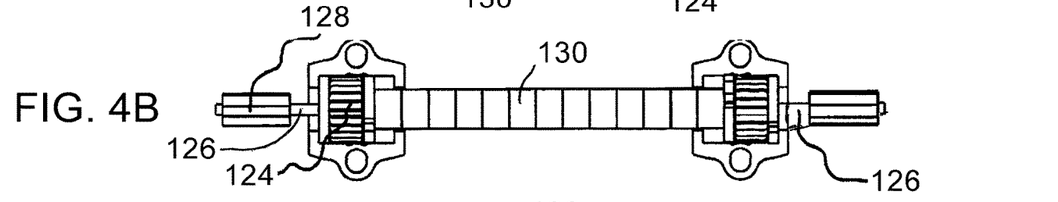

In FIG. 4B, movement of the anchor assemblies 108 (and associated vertebrae regions) toward each other generally compresses the bushings 130 of the spinal stabilization apparatus 100 and the compression springs 124 act against the outer thrust walls 120 of the sockets 112.

Figure 4C:
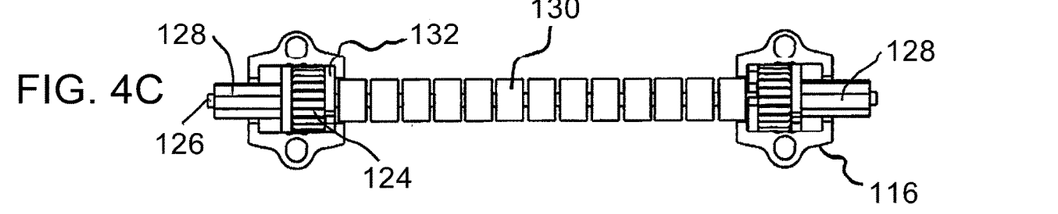

In FIG. 4C, movement of the anchor assemblies 108 (and associated vertebrae regions) away each other generally increases the distance between the bushings 130 and the compression springs 124 act against the inner thrust walls 120 of the sockets 112.

Figures 4D, 4E:
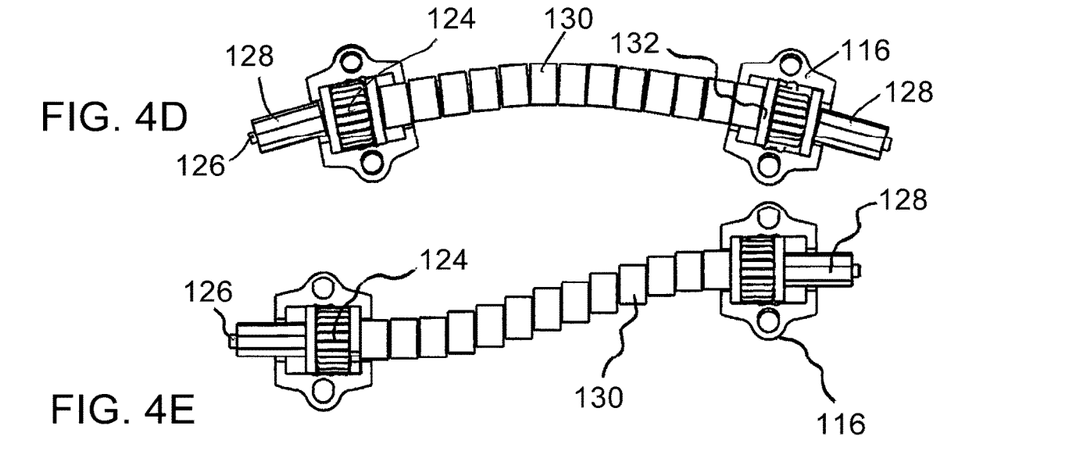

In FIG. 4D, a bending movement may reorient the anchor assemblies 108 (and associated vertebrae regions) and thus bending the cable 126 while the compression springs 124 act against the outer thrust walls 120 of the sockets 112.

In FIG. 4E, movement may shift or translate laterally the anchor assemblies 108 (and associated vertebrae regions) while the spinal stabilization apparatus 100 generally resists compression of the bushings 130 and the compression springs 124 act against the inner thrust walls 120 of the sockets 112.

Those skilled in the art will recognize that a combination of movements relative to two anchor assemblies 108 or two respective vertebrae is possible, such that the two vertebrae may move toward or apart from each other, while also reorienting and translating relative to each other. In this respect, for example, when the spinal stabilization apparatus 100 is bent and/or shaped in a 'S' curve, it is possible for thrust forces against the thrust walls 120 to occur in either direction depending upon whether anchor assemblies 108 are moving apart or toward each other.

Figure 5:
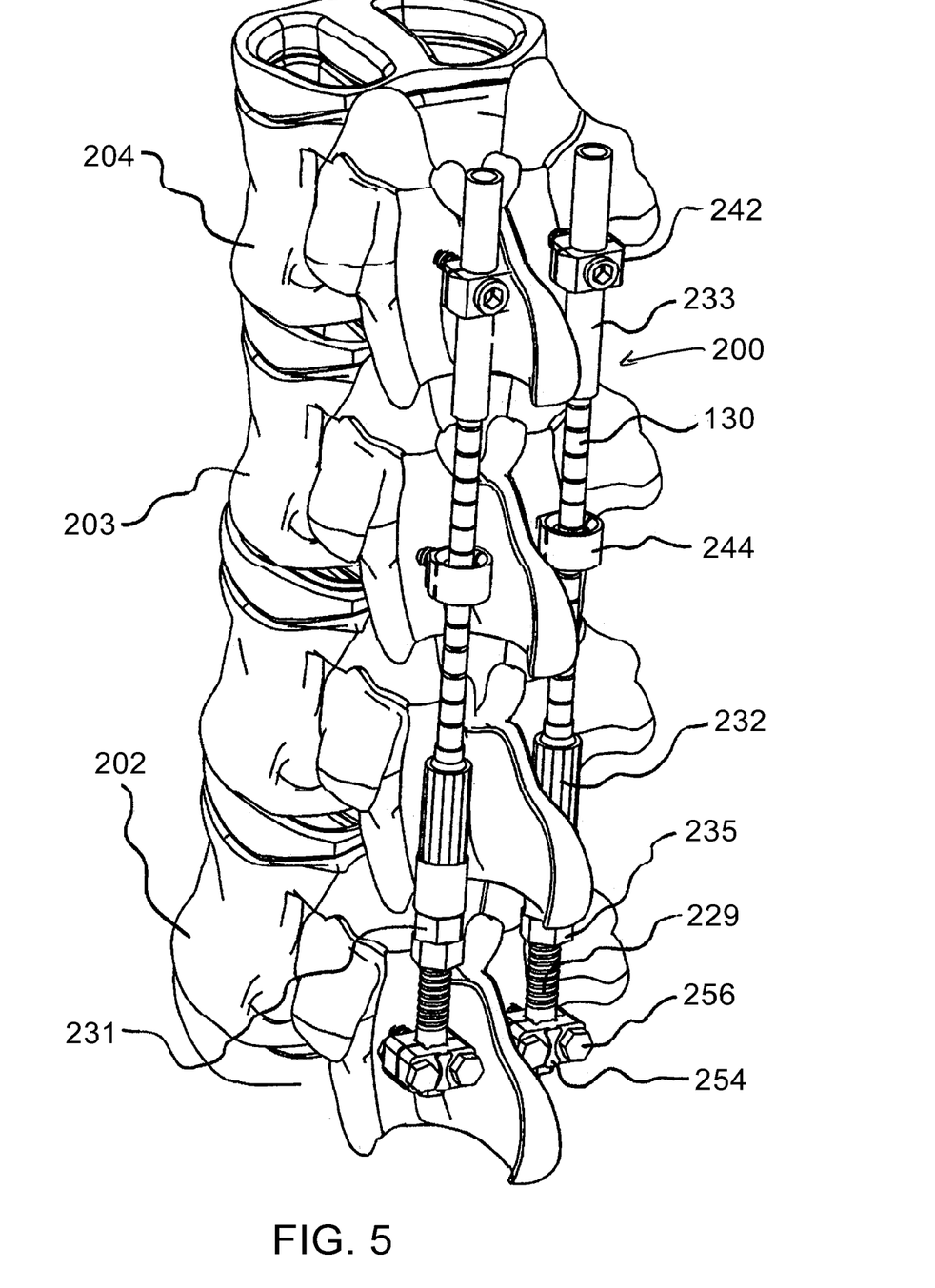
FIG. 5 is a perspective of a second embodiment of a spinal stabilization apparatus.
Figure 6:
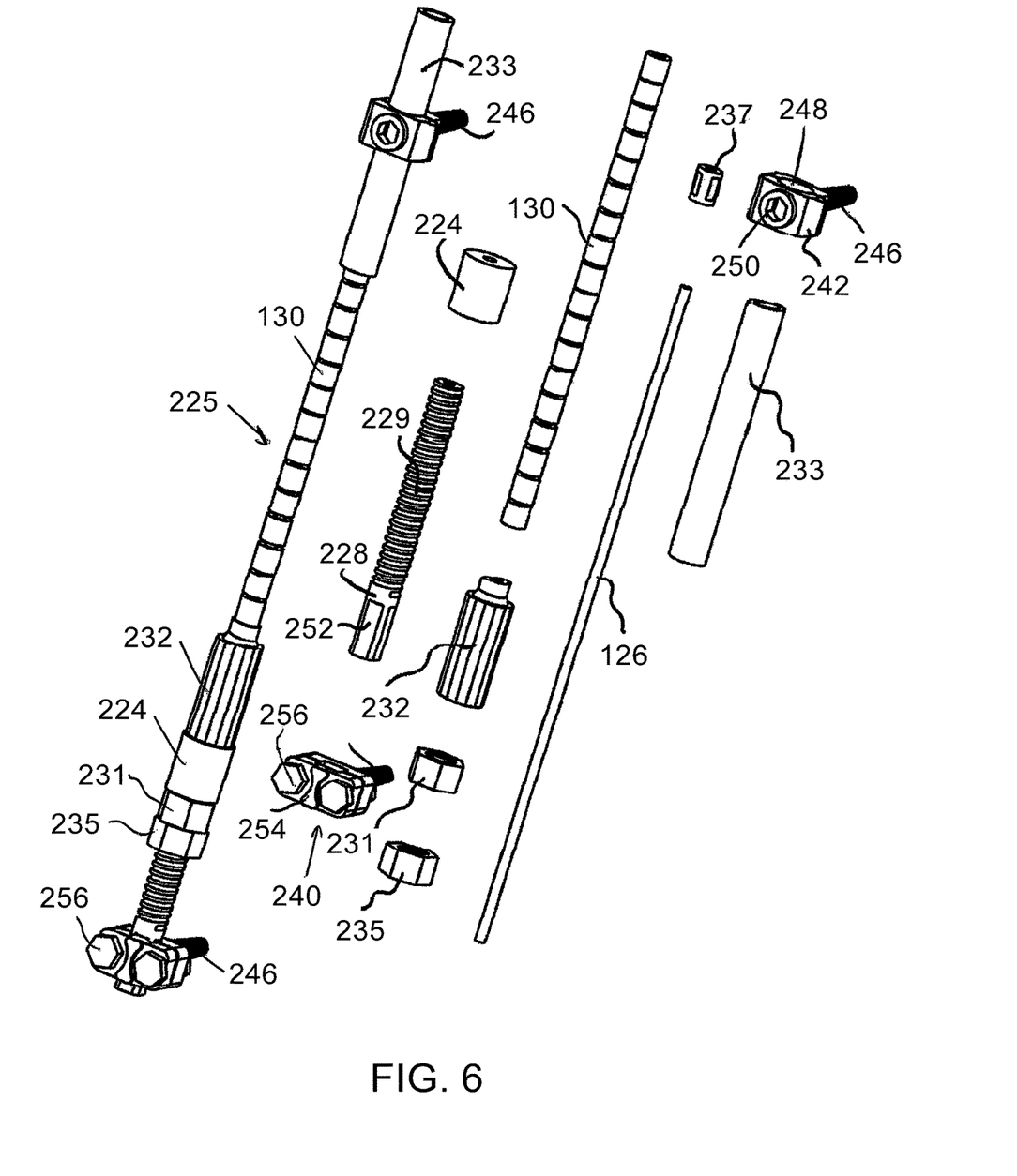
FIG. 6 is an exploded perspective view of components of the spinal stabilization apparatus illustrated in FIG. 5.
Figures 7A, 7B, 7C:
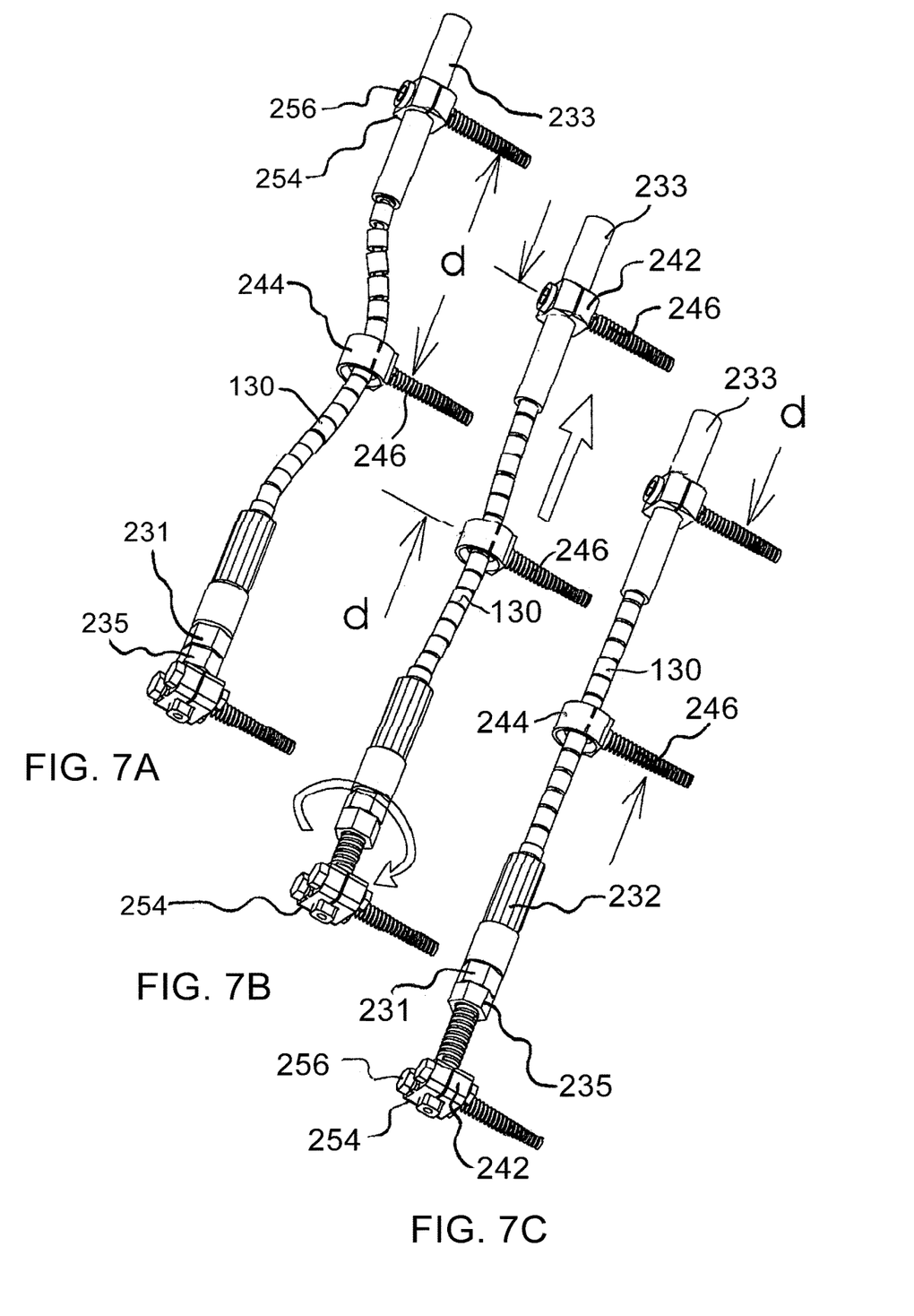
FIG. 7A-7C are perspective views of the spinal stabilization apparatus illustrated in FIG. 5 depicting configurations of the spinal stabilization apparatus under various tensional loads.

In FIGS. 5-7, a second embodiment of a spinal stabilization apparatus is generally identified by the reference numeral 200. The spinal stabilization apparatus 200 may be attached to multiple vertebrae for biasing the entire spine to a fully normal curvature. In FIG. 5, two spinal stabilization apparatus 200 are depicted attached to a portion of a spine. Like parts of the spinal stabilization apparatus 100 and 200 are identified herein by like reference numerals.

Referring now to FIG. 6, components of the spinal stabilization apparatus 200 are illustrated in an exploded view. The spinal stabilization apparatus 200 may include a cable sub-assembly 225 comprising the cable 126, bushings 130, compression spring 224, thrust bushing 232, slide tube 233 and jack screw 228. The jack screw 228 may include an external threaded portion 229. A jam nut 231 and a lock nut 235 may be threaded on the threaded portion 229 of the jack screw 228. The compression spring 224 may then be installed on the jack screw 228 in abutting contact with the jam nut 231.

Continuing with the assembly of the cable sub-assembly 225, the jack screw 228 may include an axial borehole adapted for receiving a distal end of the cable 126 for fixedly securing the cable 126 to the jack screw 228 by crimping or other means known in the art. The thrust bushing 232 may thereafter be installed onto the threaded portion 229 of the jack screw 228 in abutting contact with an end of the compression spring 224. The compression spring 244 may, for example and without limitation, comprise helical metal compression springs, urethane and/or silicone bio-compatible die stamping spring, belleville springs and/or belleville spring washers and the like. A plurality of bushings 130 may be threaded on the cable 126 in series. An end bushing 237 crimped on the opposite or second distal end of the cable 126 retains the bushings 130 on the cable 126.

One of several possible methods of installing the spinal stabilization apparatus 200 to a patient's spine will now be described with reference to FIGS. 5-7. To install the spinal stabilization apparatus 200 to the spine, anchor assembly 240 and tube slide anchor 242 are secured to the vertebrae 202 and 204, respectively. A ring pedicle screw 244 may be secured to one or more intermediate vertebrae 203. Typically, the intermediate vertebrae 203 require alignment or de-rotation for proper alignment of the spine. The anchor assembly 240, tube slide anchor 242 and ring pedicle screw 244 may be installed by securing the threaded screw portions 246 thereof to the vertebrae in a manner known in the art.

The tube slide 233 may then be secured to the tube slide anchor 242 by inserting the tube slide 233 through an opening 248 and tightening a set screw 250 and the like against the tube slide 233. Thereafter, the end bushing 237 portion of the cable sub-assembly 225 may be passed through the ring pedicle screw 244 and the end bushing 237 inserted into the tube slide 233. The opposite end portion of the cable sub-assembly 225 is rigidly secured to the anchor assembly 240. The upper end of the anchor assembly 240 is configured to engage an end portion of the jack screw 228, for example and without limitation, an end portion 252 defining a square cross section. An anchor cap 254 may clamp over the jack screw 228 by tightening cap screws 256.

After attachment of the spinal stabilization apparatus to the patient's spine, it may be adjusted by rotating the jam nut 231 to advance it toward the tube slide 233. As a consequence of rotating the jam nut 231, the bushings 130 may be compressed more or less depending upon the compressive force exerted by the compression spring 224 against the thrust bushing 232 and transmitted to the bushings 130. Typically, the bushing 130 may be experience one hundred pounds of compression along the 'stack' of bushings 130, for example, although those skilled in the art will appreciate that this compressive force is not transmitted to the vertebrae 202, 203, 204 because the ring pedicle screw 244 allows the bushings 130 to pass through without axial restraint, and the tube slide 233 allows the end bushing 237 and any number of bushings 130 to axially pass unrestricted into the tube slide 233. Effectively, as jam nut 231 is rotated, the column of bushings 130 straightens, as illustrated in FIGS. 7A-7C, thereby moving the intermediate vertebrae 203 into proper alignment with respect to anchor assembly 240 and tube slide pedicle screw 242. The vertebrae alignment may be biased over time to correct the spine curvature. Minimal post-surgery operations may be required in order to periodically rotate the jam nut 231. Alternatively, the jam nut 231 may be rotated externally by means of miniature paddles and a two directional ratchet implanted under the skin of the patient, where such paddles may be manipulated outside the patient's body in order to turn and ratchet/lock the jam nut 231 as may be required.

Figures 8A, 8B:
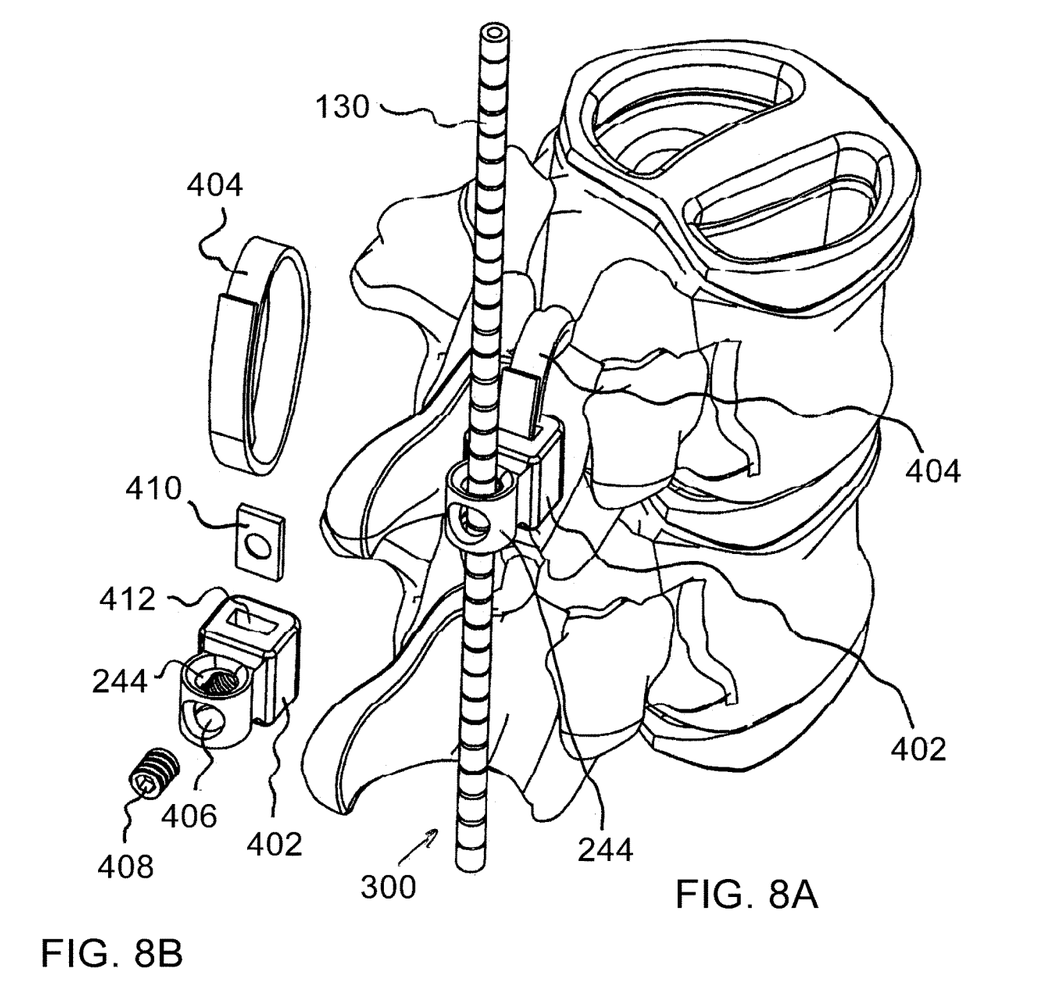
FIGS. 8A and 8B are perspective views of a third embodiment of a spinal stabilization apparatus.

Referring now to FIGS. 8A and 8B, a third embodiment of a spinal stabilization apparatus is generally identified by the reference numeral 300. As evidenced by the use of common reference numerals, the spinal stabilization apparatus 300 is similar to the spinal stabilization apparatus 200 described above with the exception that the spinal stabilization apparatus 300 includes a ring guide 402 secured to the intermediate vertebrae 203. The ring guide 402 may be secured about a portion of bony element of a patient's vertebrae by a strap 404. The ring guide 402 may include a hole 406 through which a set screw 408 may compress a thrust plate 410 against overlapping strap regions and against a base of the ring guide 402. The overlapping regions of the strap 404 may be adapted to pass through a slot 412 in the ring guide 402 and may be trimmed as required upon completion of installation. This strap means may also be employed to secure the tube slide 232 and/or first pedicle anchor 227, and may be considered less invasive as compared to threaded pedicle screws. A ring guide 402 and strap 404 may also be employed to secure the tube slide 233 and/or tube slide pedicle screw 242, and may be considered less invasive as compared to pedicle screws.

While a preferred embodiment of the invention has been shown and described, other and further embodiments of the invention may be devised without departing from the basic scope thereof, and the scope thereof is determined by the claims which follow.

The invention claimed is:

1. A spinal stabilization apparatus, comprising:
   a) at least two anchor assemblies securable to vertebrae of the spine;
   b) a cable sub-assembly removably connected to said at least two anchor assemblies, wherein said cable sub-assembly includes a plurality of bushings threaded in series on a cable, said plurality of bushings disposed between end bushings fixedly secured to opposite distal ends of said cable;
   c) each said anchor assemblies including a socket fixed to an upper end of a pedicle screw, said socket including axially spaced apart end walls transverse to a longitudinal axis of said socket, said anchor assembly further including a cap member separable from said socket; and
   d) biasing members threaded on said cable, said biasing members comprising compression springs disposed between said end walls of a respective said socket.

2. The apparatus of claim 1 wherein said cable sub-assembly includes a jack screw fixedly secured to a distal end of said cable.

3. The apparatus of claim 2 wherein said jack screw includes an externally threaded portion, a stop member threaded on said threaded portion, and wherein a respective said biasing member is in abutting contact with said stop member.

4. The apparatus of claim 1 wherein said anchor assembly includes a slide tube anchor and a slide tube secured to said slide tube anchor.

5. The apparatus of claim 4 wherein said slide tube is securable to a vertebra by a strap.

6. The apparatus of claim 1 including a ring pedicle screw securable to a vertebra, said ring pedicle screw disposed between said at least two anchor assemblies.

7. The apparatus of claim 1 including a ring guide securable to a vertebra by a strap.

8. The apparatus of claim 1 including a thrust bushing threaded on said cable in abutting contact with a respective said biasing member.

9. A spinal stabilization apparatus, comprising:
   a) at least two anchor assemblies securable to vertebrae of the spine;
   b) a cable sub-assembly removably connected to said at least two anchor assemblies, wherein said cable sub-assembly includes a plurality of bushings threaded in series on a cable, said plurality of bushings disposed between end bushings fixedly secured to opposite distal ends of said cable;
   c) each said anchor assemblies including a socket fixed to an upper end of a pedicle screw, said socket defining a cavity having a longitudinal axis concentric with said cable, said socket including axially spaced apart end walls transverse to said longitudinal axis of said cavity, said anchor assembly further including a cap member separable from said socket; and
   d) biasing members threaded on said cable, said biasing members disposed between said end walls of a respective said socket.

10. A spinal stabilization apparatus, comprising:
    a) at least two anchor assemblies securable to vertebrae of the spine;
    b) a cable sub-assembly removably connected to said at least two anchor assemblies, wherein said cable sub-assembly includes a plurality of bushings threaded in series on a cable, said plurality of bushings disposed between end bushings fixedly secured to opposite distal ends of said cable;
    c) each said anchor assemblies including a socket fixed to an upper end of a pedicle screw, said socket including axially spaced apart end walls transverse to a longitudinal axis of said socket, said anchor assembly further including a cap member separable from said socket; and
    d) helical compression springs threaded on said cable, said compression springs disposed between said end walls of a respective said socket.

\* \* \* \* \*